(12) United States Patent
Hof et al.

(10) Patent No.: US 7,713,059 B2
(45) Date of Patent: May 11, 2010

(54) SELF ADJUSTING INSTRUMENT

(75) Inventors: Rephael Hof, Kfar Yona (IL); Ehud Teperovich, Raanana (IL); Amir Meir Zilbershtain, Moshav Yad Rambam (IL)

(73) Assignee: Redent-Nova Ltd., Ra'Anana (IL)

( * ) Notice: Subject to any disclaimer, the term of this patent is extended or adjusted under 35 U.S.C. 154(b) by 386 days.

(21) Appl. No.: 10/573,932

(22) PCT Filed: Jan. 24, 2005

(86) PCT No.: PCT/IL2005/000086

§ 371 (c)(1),
(2), (4) Date: Nov. 2, 2006

(87) PCT Pub. No.: WO2005/070320

PCT Pub. Date: Aug. 4, 2005

(65) Prior Publication Data

US 2007/0054238 A1    Mar. 8, 2007

(30) Foreign Application Priority Data

Jan. 26, 2004    (IL) .................................... 160074

(51) Int. Cl.
  *A61C 5/02* (2006.01)
(52) U.S. Cl. ...................... 433/102; 433/224
(58) Field of Classification Search ........... 433/102, 433/224, 165, 166, 141, 143, 144, 164; 408/204, 408/205, 207
See application file for complete search history.

(56) References Cited

U.S. PATENT DOCUMENTS

| | | | |
|---|---|---|---|
| 3,578,745 A | 5/1971 | Garnier | |
| 4,019,254 A * | 4/1977 | Malmin | ................. 433/102 |
| 4,190,958 A | 3/1980 | Martin et al. | |
| 4,830,615 A | 5/1989 | Goldstein et al. | |
| 5,165,893 A | 11/1992 | Thompson | |
| 5,501,597 A | 3/1996 | Wilson | |
| 5,533,897 A | 7/1996 | Zdarsky | |

(Continued)

FOREIGN PATENT DOCUMENTS

EP    1174094    1/2002

(Continued)

OTHER PUBLICATIONS

Saunders et al., "Technical standard of root canal treatment in an adult Scottish sub-population", British Dental Journal (1997); 182(10): 382-386.

(Continued)

*Primary Examiner*—Ralph A Lewis
*Assistant Examiner*—Yogesh Patel
(74) *Attorney, Agent, or Firm*—Mark M. Friedman

(57) ABSTRACT

The invention is an instrument for cleaning and/or shaping and/or widening a channel that exists in or through a solid object. The design of the instrument the superelastic and shape memory properties of the material from which it is made, allow the inner volume enclosed by the instrument, its outer contour, or both to change as a result of the forces exerted upon it while working, thereby shaping the instrument to the three-dimensional contour of the channel. A preferred embodiment of the instrument is an endodontic file for use in the cleaning, shaping, and widening stages of a root canal procedure.

23 Claims, 14 Drawing Sheets

U.S. PATENT DOCUMENTS

| | | | |
|---|---|---|---|
| 5,685,716 A | | 11/1997 | Linkow |
| 5,752,825 A | * | 5/1998 | Buchanan .................... 433/32 |
| 5,897,316 A | * | 4/1999 | Buchanan ................... 433/102 |
| 5,941,706 A | * | 8/1999 | Ura ........................... 433/165 |
| 6,340,027 B1 | | 1/2002 | Hagne et al. |
| 6,343,929 B1 | | 2/2002 | Fischer |
| 6,443,730 B2 | | 9/2002 | Davidson |
| 6,464,498 B1 | | 10/2002 | Pond |
| 6,575,748 B1 | | 6/2003 | Filhol |
| 6,589,052 B1 | | 7/2003 | Wilcko |
| 6,746,245 B2 | | 6/2004 | Riitano et al. |
| 6,966,774 B2 | | 11/2005 | Brock et al. |
| 6,981,869 B2 | | 1/2006 | Ruddle |
| 7,137,815 B2 | | 11/2006 | Matsutani et al. |
| 2003/0044752 A1 | | 3/2003 | Fischer et al. |
| 2003/0105469 A1 | | 6/2003 | Karmon |
| 2003/0211442 A1 | * | 11/2003 | Abel .......................... 433/102 |

FOREIGN PATENT DOCUMENTS

| | | | |
|---|---|---|---|
| RU | 2143244 C1 | | 12/1999 |
| WO | WO9015683 | * | 6/1989 |

OTHER PUBLICATIONS

Tan et al., "The Quality of Apical Canal Preparation Using Hand and Rotary Instruments with Specific Criteria for Enlargement Based on Initial Apical File Size", Journal of Endodontics (2002); 28(9): 658-664.

Wu et al., "Prevalence and extent of long oval canals in the apical third", Endodontics (2000); 89(6): 739-743.

Wu et al., "A primary observation on the preparation and obturation of oval canals", International Endodontic Journal (2001); 34: 137-141.

PCT International Search Report, PCT Application No. PCT/IL2005/000086, Jun. 1, 2005, 5 pages.

Written Opinion, PCT Application No. PCT/IL2005/000086, Jun. 1, 2005, 6 pages.

* cited by examiner

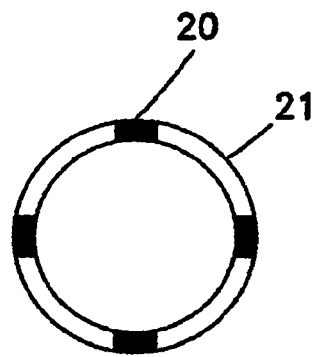
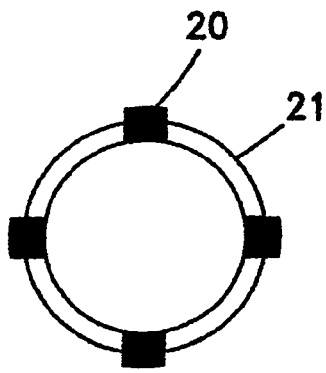
Fig. 11A        Fig. 11B
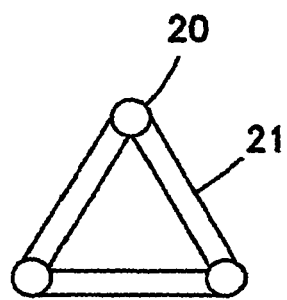
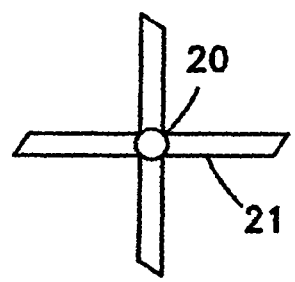
Fig. 11C        Fig. 11D
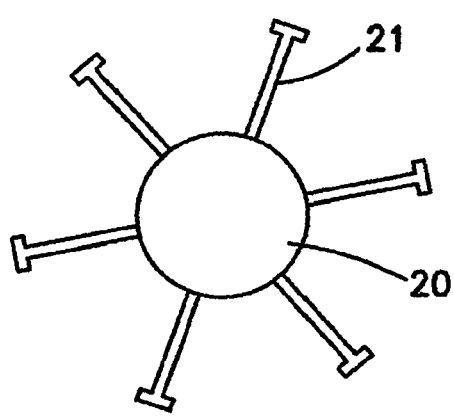
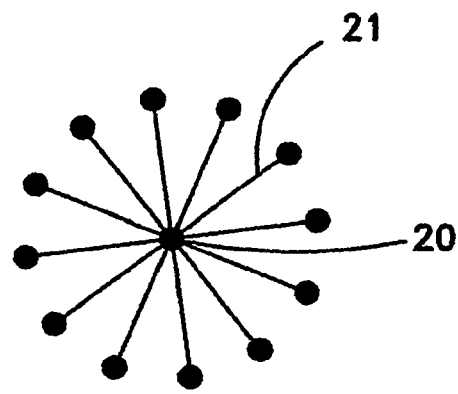
Fig. 11E        Fig. 11F

SELF ADJUSTING INSTRUMENT

This application is the National Stage of International Application No. PCT/IL2005/000086 filed on Jan. 24, 2005, which claims priority to Israeli application no. 160074 filed on Jan. 26, 2004, and which application(s) are incorporated herein by reference.

FIELD OF THE INVENTION

The present invention is related to the field of tools. Specifically the present invention relates to an instrument for cleaning and/or shaping and/or widening a channel, existing in or through a solid object.

BACKGROUND OF THE INVENTION

Publications and other reference materials referred to herein, including references cited therein, are incorporated herein by reference in their entirety and are numerically referenced in the following text and respectively grouped in the appended Bibliography which immediately precedes the claims.

There are many situations in which it is required to use an instrument for cleaning out and/or shaping and/or widening a channel that exists in or passes through a solid object. One of the best examples illustrative of the problem and of the shortcomings of the prior art is from the field of dental instruments, specifically root canal procedures. Root canal procedure is one of the most demanding tasks for a dental surgeon. Root canal treatment consists of two stages: (a) shaping, cleaning, and widening of the root canal and (b) obturation of the canal space. The first stage is aimed at removing all tissue remnants, shaping the canal space and disinfecting it, while the second stage is aimed at sealing the root canal and preventing its recontamination. Failure to achieve either of those goals may result in persistent apical periodontitis—associated with periapical bone resorption and occasional or chronic suppuration.

In the simplest case, in which the canal is relatively straight and has a relatively uniform circular cross-section, the work is carried out by starting with a small diameter instrument (known as a dental file) and replacing it with a series of increasingly larger diameter files until the desired final diameter of the canal is attained. If the canal is not straight, using the conventional stainless steel files will most probably result in a poor quality of treatment. In cases in which the curvature is not too great, nickel titanium alloy files are able to adapt themselves to the longitudinal curvature of the canal; thus achieving better results; however existing nickel-titanium alloy files cannot adapt themselves to changes in the shape or diameter of the canal, therefore a series of files must be used to clean out a canal as is the case with stainless steel files. Also the use of any type of existing file in a canal having non uniform or non circular cross-section results in a canal that is either not completely cleaned out or one having a circular cross-section, the uniform diameter of which is at least as large as the maximum width of the original canal.

The anatomy of a tooth is shown in FIG. 1. Topographically tooth 1 is divided into two sections. The crown 2, covered by enamel 4, is the visible part of the tooth. The root 3 is below the gums and anchors the tooth in place in the jaw bone. Within the dentin 6, which comprises the principal mass of the tooth, is located the pulp chamber 5 and one or more root canals 7, both of which are filled with pulp 8.

FIGS. 2A to 2C illustrate the major steps of the root canal procedure. In the first step (shown in FIG. 2A) part of the crown is removed and the pulp is cleaned out of the pulp chamber. In the second step (FIG. 2B) the openings of the root canals are widened. Then (FIG. 2C) the canal system is shaped, cleaned, and widened, removing all pulp particles and infection. In a final step (not shown in the figures) the clean and disinfected root canals are obturated.

Endodontic failures are more common than the profession is willing to acknowledge. The commonly quoted success rates are based mainly on studies carried out in teaching institutes and/or by endodontists. Nevertheless, surveys carried out on the general public indicate that in association with up to 58% of the endodontically treated teeth a periapical lesion was evident (1).

This represents, most probably, a poor quality of treatment (1); nevertheless, it may also represent a basic flaw in the common approach to root canal treatment. Root canals are usually perceived as having a gradually tapering diameter with a round cross section (FIG. 3A). This may be true for many upper anterior teeth; however, it is far from reality in many of the bicuspids and molars. In these teeth ribbon-like root canals, with a flat cross section (FIG. 3B) are common (2). The flat dimension of these canals is at the bucco-lingual plane, which is not seen on a radiograph, and usually has its maximal width at 5 mm from the apex. This anatomy is especially pronounced in the second upper bicuspids, in distal roots of lower molars, as well as in many canines and lower incisors. Additionally, canals with a tear-shaped cross section (FIG. 3C) are common in roots that have two canals, such as the mesial roots of lower molars and those of upper first bicuspids as well as in many of the mesio-buccal roots of upper molars. The fact that all of these anatomical variations are not seen on a regular periapical radiograph is one of the reasons for the common misconception and presents a major obstacle in achieving the goal of high quality endodontic treatment.

The traditional, common, approach for cleaning, widening, and shaping root canals utilizes hand files having round cross-sections and a standardized cylindro-conic shape. Sequential use of files of increasing diameter, with intermitted flushing with antiseptic solution, results in a canal in which a cylindro-conic gutta-pecha cone may intimately be fitted in the apical part of the canal and used as a "master cone". With the proper paste type sealer and accessory cones they are expected to seal the apical part of the canal. The common cleaning, widening, and shaping procedures are designed to adapt the apical part of the root canals to the form of these standardized master cones.

This common concept is based on the image of a root canal that has a round cross section, which may gradually be enlarged by round files to the shape of a standardized master cone. Although suitable for anterior teeth, when applied in many posterior root canals, this approach may often lead to failure. Cleaning, widening, and shaping a flat root canal with round files will frequently leave a remaining buccal and/or lingual recesses along the root canal filling, untouched and full of tissue remnants, bacteria, or both (3,4). This will inevitably result in failure. Recent studies indicate that this problem is much more common than previously appreciated (2, 3).

When using traditional hand-held stainless steel files some of these recesses are inevitably only partially cleaned. In FIG. 4 is shown a set of stainless steel K-files. A great deal of experience is necessary to choose the proper length and diameter as the canal is cleaned out from the top to the bottom. When the root canal curves it is only possible to follow the curvature by increasing the diameter of the canal. This problem is illustrated in FIG. 5A. If the curvature of the canal becomes to great, generally near the apex of the canal, then one of two undesirable situations arises. The first, shown in FIG. 5B, is that the process is terminated resulting in creation of a ledge in the canal and debris in the untreated lower part of the canal. The second alternative, shown in FIG. 5C, is that the procedure continues until perforation of the tooth occurs, also resulting in a false canal or apex enlargement. One other major difficulty encountered during root canal treatment is shown in FIG. 5D; if one of the solid files breaks and can not be removed, a not infrequent occurrence, then the root canal treatment fails and the tooth is usually removed.

The hand-held stainless steel instruments are currently gradually being replaced by nickel titanium rotary files. As in the case of K-files, current leading nickel titanium rotary files are used as series of instruments with gradually enlarging diameters but, unlike the stainless steel files, are able to adapt longitudinally to the canal shape. Nickel titanium rotary files are more efficient and allow the operator to complete a case in a somewhat shorter time. Unfortunately, this efficiency has a price: the prepared canal is of a perfect round cross section and the cleaning of the recesses in flat and tear-shaped canals is not done.

Recognition of the above problem has led some professional authorities to consider a further enlargement of the apical part of the canals, to a diameter that will include the flat remaining parts. The preparation of a root canal by enlargement for root canals having round, flat, and tear-shaped cross-sections is shown schematically in FIGS. 6A, 6B, and 6C respectively. Such enlargement could not be safely done in bent root canals with traditional stainless steel instruments because of their rigidity (3). Rotary nickel titanium files made it possible to enlarge bent canals in a mesial root of a lower molar to accept a No. 45-50 gutta-percha master cone. Nevertheless, this approach has two short comings: it may frequently lead to either unwanted excessive local thinning of the remaining root canal wall (2) or to the use of a single-cone root canal filling in the apical third of the canal. The first may lead to a higher frequency of vertical root fractures, while the second was discarded long ago for its inferior sealing abilities. Furthermore, in many cases the diameter required to really include the recesses is so large that it will cause a perforation of the canal wall (2) (see FIG. 6B and FIG. 6C).

The issue of cleaning, widening, shaping, and obturation of root canals with non-round cross sections does not currently have an adequate, efficient solution.

It is therefore a purpose of the current invention to provide an instrument that is capable of changing its interior volume, contour, or both during use in cleaning and/or shaping and/or widening a channel, existing in or through a solid object, in order to shape itself to the channel's three-dimensional contour.

It is another purpose of the current invention to provide an endodontic file that is capable of cleaning and shaping and widening root canals having circular and/or non-circular cross sections.

It is another purpose of the current invention to provide an endodontic file whose contour varies during use thus allowing the use of a single file for an entire root canal procedure.

It is yet another purpose of the current invention to provide an endodontic instrument that is sufficiently flexible to allow it to adapt itself longitudinally to the curvature of the root canal up to its apical end.

It is still another purpose of the current invention to provide an endodontic instrument through which antiseptic solution can continuously flow into the root canal while working.

It is a further purpose of the current invention to provide an endodontic file that has significantly greater endurance and strength than existing instruments used to perform root canal treatments.

It is another further purpose of the current invention to provide an endodontic file that requires significantly less time to perform root canal treatments than existing instruments.

It is a still further purpose of the current invention to provide an endodontic instrument that is significantly easier to use and has a significantly shorter learning curve than existing instruments used to perform root canal treatments.

Further purposes and advantages of this invention will appear as the description proceeds.

SUMMARY OF THE INVENTION

The present invention can be realized in many different embodiments and has applications in many fields in which it is necessary to clean out and/or shape and/or widen a channel, existing in or through a solid object Examples of such applications can be found, for example, in such widely differing fields as drilling for oil, dental surgery, and material machining. In order to best illustrate the many advantages of the instrument of the invention over existing tools, a specific embodiment of the invention for use in dental root canal treatment, one of the most demanding applications for instruments of this type, has been chosen as an illustrative and non-limiting example to be described herein.

The preferred embodiment of the endodontic instrument of the invention, known herein as the SAF (self adjusting file) is a nickel titanium instrument of a unique self adjusting design. The SAF has an original round cross-section to which it always tries to return as a result of superelastic properties that are given to it. Simultaneously this property combined with its unique geometry gives it an extreme ability to adapt itself to the shape of the canal walls. When inserted into a narrow canal it will have a contour narrower than its original one, which will gradually increase with use, thus allowing it to be used as a single instrument for the whole root canal procedure. Moving the instrument of the invention in the root canal, preferably by rotating the instrument but optionally by moving it back and forth in a direction essentially parallel to the longitudinal axis of the canal or by causing it to vibrate, will result in the removal of a layer from all inner surfaces of the canal, to which it adapts itself, while gradually attempting to return to its original round shape. The instrument will thus perform an ideal shaping, widening, and cleaning, without unwanted localized thinning of the root wall.

The unique design of the instrument allows it to adapt itself both longitudinally and in the cross section and thus follow the original three dimensional shape of the root canal. Thus, a canal with a round cross section will be enlarged as round, while a flat canal will be enlarged as a flat canal of greater dimensions. Even the trickiest canals, those with a tear shaped cross section, will essentially maintain their original shape. Further the design of the instrument allows it to achieve different shapes and dimensions along the length of the canal, thereby allowing effective cleaning of the entire canal without excessive widening of the canal walls. The method of the prior art to extensively enlarge root canals in order to include in their diameter the flat or tear-shaped recesses is thus eliminated.

Due to the special open and/or hollow design, antiseptic solution can continuously flow into the root canal while working, thus saving valuable time and improving the debridement and disinfection procedures. The constant flow also increases the efficiency of filing and prevents clogging the canal with dentin-mud and debris.

The structural design of the self adjusting file of the invention allows top elasticity. In the extreme case of an instrument failure and breakage inside the canal, specially designed extractors can be used to easily remove the separated part of the SAF, no matter what the position or depth of the broken-off part is in the root canal.

In a first aspect the present invention provides an instrument for cleaning and/or shaping and/or widening a channel that exists in or through a solid object. The instrument of the invention is characterized in that its inner volume, contour, or both changes during use in order to shape it to the three-dimensional contour of said channel. In particular the shape of the perimeter of the instrument adjusts during use to conform to the perimeter of the local cross section of the channel at each radial plane located along the length of the instrument that is inserted into the channel.

The instrument of the present invention can be made from a superelastic material and a material which either has or has been treated to give it shape memory properties. In a preferred embodiment, the instrument of the invention is made from a nickel titanium alloy.

Preferably a single instrument is inserted into the channel and used for the entire procedure of cleaning and/or shaping and/or widening the channel before being withdrawn. In some applications, more than one file is used to clean, and/or shape, and/or widen the channel. If the instrument breaks inside the channel, the broken piece can be withdrawn from without damage to the object containing the channel.

In a preferred embodiment of the instrument of invention, its body is comprised of one or more longitudinal elements and one or more circumferential elements. The longitudinal and circumferential elements can have a three-dimensional shape chosen from the group comprising: blade shaped, polygonal prism shaped, rod shaped, curved shaped, and round shaped elements. The cross-sectional shape of the longitudinal and circumferential elements can be chosen from the group comprising: polygonal, round, and curved shapes. The longitudinal elements and the circumferential elements can be straight or curved. In a preferred embodiment, the number of longitudinal elements is at least one and the circumferential elements are distributed along the longitudinal axis of said instrument. In another embodiment, the number of longitudinal elements is at least one and the circumferential elements are distributed along the longitudinal axis of the instrument. The circumferential elements in a given radial plane define the local cross-sectional shape of the instrument.

In a preferred embodiment of the instrument of the invention, the longitudinal and circumferential elements define the instrument's three-dimensional shape. That shape being that of a body with an empty space surrounding the longitudinal axis and bounded radially by a wall having an open lattice-like structure.

In preferred embodiments of the instrument of the invention, at least a part of the outer surface of the instrument is constructed or modified in such a way as to allow the instrument to remove material from the wall of the channel when relative motion takes place between it and the wall. The relative motion can be rotational, translational, vibrational, or a combination of two or more of these types of motion. In one embodiment, at least part of the outer surface of the instrument is coated with a coating of an abrasive material, which can be for example, diamond powder, titanium nitride, or tungsten carbide. In other embodiments, at least part of the outer surface of the instrument of the invention is roughened, comprises numerous small teeth, or comprises a cutting edge.

Preferably, fluid can flow into the channel and/or debris resulting from the cleaning and/or shaping and/or widening can be removed from the channel while the instrument of the invention is inserted and working in the channel. The fluid can flow and/or the debris can be removed via the interior of the instrument and/or, in other embodiments via the space between the wall of the channel and the outer surface of the instrument.

In preferred embodiments of the instrument of the invention, a uniform amount of material is removed from the wall of the channel, along the entire insertion length of the instrument in the channel, during the procedure of cleaning and/or shaping and/or widening the channel. In other embodiments, the instrument can be constructed such that different amounts of material are removed from the channel wall at different locations along the insertion length of the instrument. The instrument of the invention can be inserted into the channel such that it passes through the entire length or only a portion of the entire length of the channel.

In preferred embodiments of the instrument of the invention, the cross-sectional shape of the channel, along the entire insertion length of the instrument, is essentially the same after the procedure of cleaning and/or shaping and/or widening the channel as it was before the procedure.

Another embodiment of the instrument of the invention comprises a long narrow balloon, which is inserted into the channel and then inflated.

Preferred embodiments of the instrument of the invention are endodontic files. In this case, the channel is a root canal, and cleaning and/or shaping and/or widening of the channel comprises the cleaning, shaping, and widening stage of a root canal procedure.

In another aspect, the present invention supplies a method of using the instrument of the invention for cleaning and/or shaping and/or widening a channel that exists in or through a solid object. The method comprises the following steps:
  inserting the instrument into the channel;
  causing relative motion between the instrument and the wall of the channel;
  optionally, removing the debris resulting from the cleaning and/or shaping and/or widening from the channel while the relative motion takes place;
  optionally, causing fluid to flow into the channel while the relative motion takes place; and
  removing the instrument from the channel when the cleaning and/or shaping and/or widening have been completed.

In the case in which the instrument of the invention is an endodontic file, the method of cleaning, and/or shaping, and/or widening a root canal comprises the following steps:
  inserting the file into the root canal;
  causing the file to move relative to the wall of the root canal;
  optionally, removing the debris resulting from the cleaning, shaping, and widening from the root canal while the file moves relative to the wall of the root canal;
  optionally, causing fluid to flow into the root canal while the file moves relative to the walls of the root canal; and
  removing the file from the root canal when the cleaning, shaping, and widening have been completed.

All the above and other characteristics and advantages of the invention will be further understood through the following illustrative and non-limitative description of preferred embodiments thereof, with reference to the appended drawings.

BRIEF DESCRIPTION OF THE DRAWINGS

FIGS. 11A to 11F show cross-sections of examples of different embodiments of the instrument of the invention.

DETAILED DESCRIPTION OF PREFERRED EMBODIMENTS

In general, the channels to be widened and/or cleaned and/or shaped by the instrument of the invention are relatively long and narrow. These channels will be described hereinbelow in terms of a single "longitudinal axis", which is the line defined by the loci of the center points of the channel along its length, and a multitude of "radial axes", wherein each such radial axis is defined by a line originating at a point on the longitudinal axis and perpendicular to the longitudinal axis at that point. Rotation of a given radial axis around its origin defines the localized "radial plane". The direction essentially parallel to the longitudinal direction will be known as the "longitudinal direction" and the direction essentially parallel to one of the radial axes will be known as the "radial direction". Because the instrument of the invention conforms to the shape of the canal similar terminology will be used to describe the principal axes of the instrument.

The instrument of the invention can be inserted completely to the end of the channel or only partially into the channel, in which case only part of the channel will be widened and/or shaped and/or cleaned. The length of the instrument that is inserted into the channel is known as the "insertion length" which term also indicates the depth of the channel that is worked on by the instrument.

As an illustrative, but non-limitative, example of the instrument of the invention embodiments of an endodontic file for performing root canal treatments will be described hereinbelow.

The preferred embodiment of the endodontic instrument of the invention, known herein as the SAF (self adjusting file) is a rotary nickel titanium instrument of a unique design. While current leading rotary files must be used as series of instruments with gradually enlarging diameters, the SAF is used as a single instrument for the whole procedure. When inserted into a narrow canal, whose nominal diameter is less than its own nominal diameter, the instrument is compressed, its superelastic property allowing it to adapt itself to the cross-sectional shape of the walls of the canal in each radial plane along the longitudinal axis of the canal. Rotating in the canal it removes tissue and debris from the canal and the canal wall. As the debris is removed from the canal wall, the super elastic property of the SAF causes it to gradually expand with time in the radial direction while continually maintaining contact with the canal wall at every point. Thus material is uniformly removed from the dentinal walls of the canal until the desired nominal diameter is achieved.

Figure 7A:
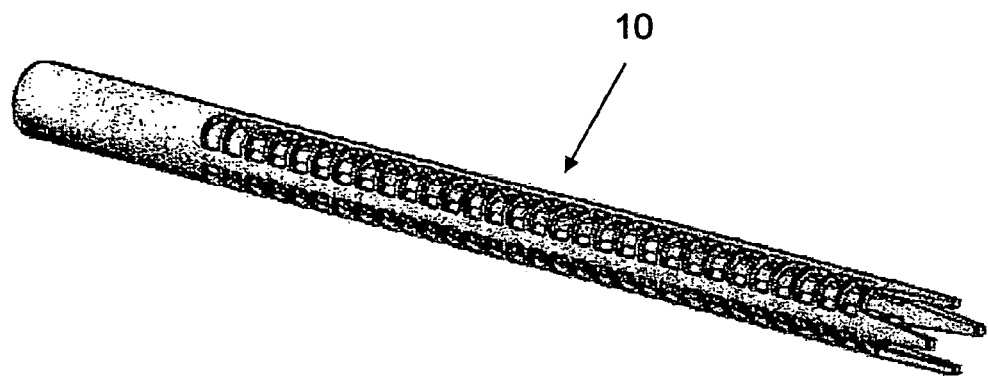
FIGS. 7A, 7B, and 7C are respectively perspective, front, and flattened-out, views of the instrument of the invention.
Figure 7B:
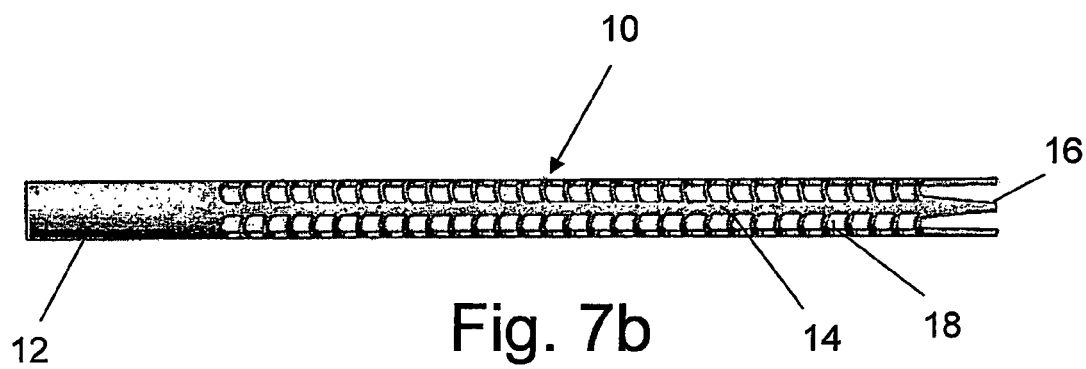
Figure 7C:
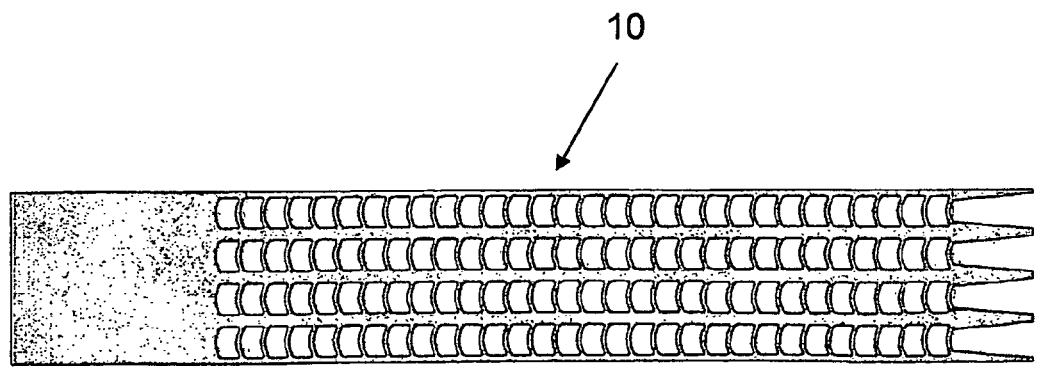

A preferred embodiment of the SAF is shown respectively in perspective, front, and flattened out, views in FIGS. 7A, 7B, and 7C. The SAF 10 is made of a nickel titanium alloy (Nitinol) and originally is given a cylindrical shape. The walls of the upper end, the neck 12, are solid and are gripped by either the dental hand piece or are attached to a handle for manual use. The main part of the body of the SAF is an open, lattice-like structure made up of longitudinal elements 14, that run the length of the instrument from neck to tip 16 and short circumferential elements 18 that connect adjacent longitudinal elements. In the preferred embodiment shown in the figures, there are four longitudinal elements and the circumferential elements, in their undeformed state are arcs of a circle. In a radial plane containing circumferential elements, the circumferential elements that lie in that plane define the cross-sectional shape of the instrument in that plane. Both the circumferential and longitudinal elements have a flat rectangular blade-like cross section. After manufacture, the Nitinol cylinder is constrained in a mold and heat treated to give it its shape memory property while changing its shape to cylindrical-conic.

The surfaces of the instrument of the invention that are in contact with the walls of the canal are treated in some way to enable them to remove material from the wall as the instrument rotates. One possible treatment is to coat the surfaces with an abrasive material such as, for example, diamond powder, titanium nitride, and tungsten carbide, that will remove dentin from the canal wall by friction as the SAF is rotated, thus cleaning out and enlarging the inside of the root canal. In other embodiments, the surfaces in contact with the wall of the canal can be manufactured with roughened surfaces comprising, for example numerous small teeth as in a file or a rasp. Alternately, these surfaces can comprise a cutting edge similar to the edge on a drill bit. In some embodiments of the instrument of the invention, the surfaces in contact with the canal wall can be relatively smooth and abrasive slurry can be introduced into the canal to be trapped between the instrument and the wall.

The material scraped from the wall of the canal passes through the openings in the lattice structure of the body of the SAF into the hollow interior from which it can easily be removed by rinsing or suction without stopping rotation of the instrument or withdrawing it from the root canal. In other embodiments, the debris can also be removed via the space between the canal wall and the instrument. The design allows for fluids, such as antiseptic or saline solution, to continuously flow into the root canal, either through the center of the instrument or between the outer surface of the instrument and the canal wall, while the instrument is working, thus saving valuable time and improving the debridement and disinfection procedures. The constant flow also increases the efficiency of filing and prevents clogging the canal with dentin-mud and debris. Another advantage of the hollow structure of the SAF is that, in the extreme case of instrument failure and breakage inside the canal, the separated part of the instrument of the invention can be easily and safely removed, using specially designed extractors, no matter what the position of the broken piece of the instrument in the root canal.

Figure 10:
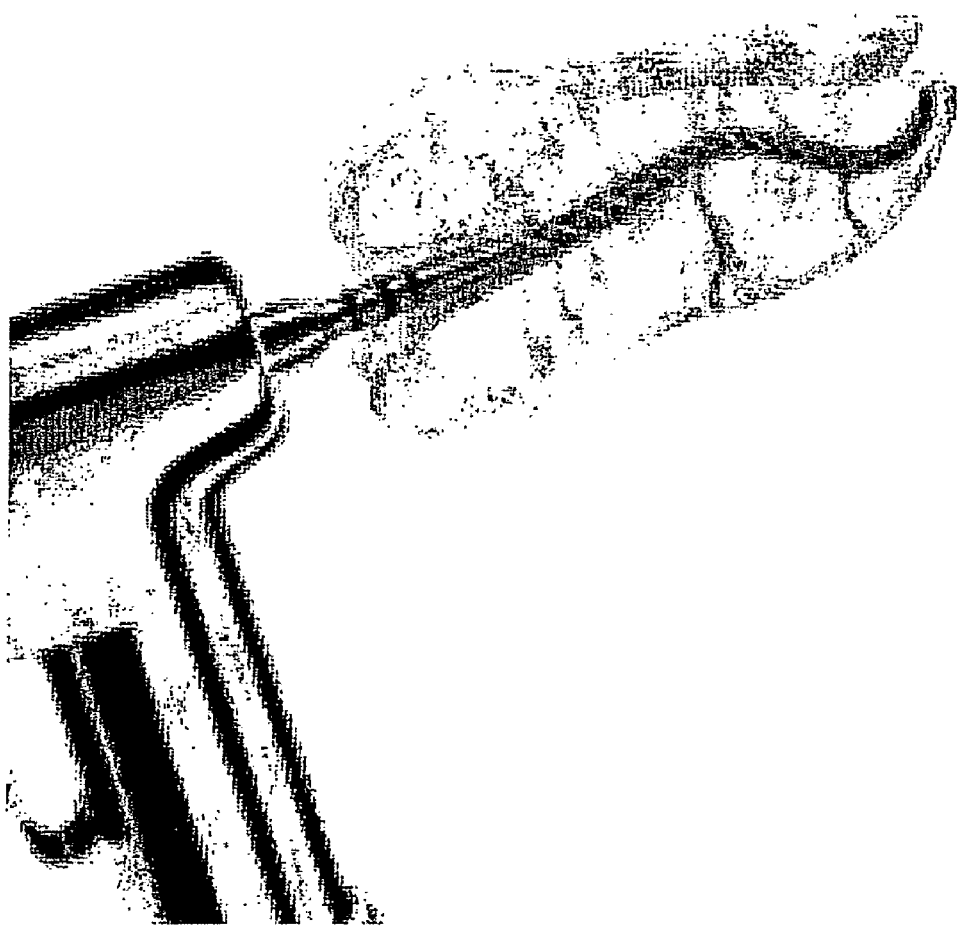
FIG. 10 shows how the instrument of the invention adapts its shape as it is inserted up to the apical end of the root canal.

After part of the crown is removed and the pulp is cleaned out of the pulp chamber, and a sufficient access to the canal is obtained the SAF is inserted into the root canal. As the instrument is pushed into the canal, its superelasticity allows it to be guided to the apical end of the root canal by following the path of least resistance (through the pulp rather than the much harder dentine). Prior art nickel titanium files can also adapt themselves to the canal shape longitudinally but are unable to change their volume and contour as can the SAF. Additionally the solid structure of the prior art files makes them less flexible than the hollow lattice-like structure SAF. In FIG. 10 is shown the SAF adapting its shape as it is inserted up to the apical end of the root canal.

The instrument is now moved relative to the walls of the root canal in order to carry out the cleaning, widening, and shaping process. The motion can be longitudinal, i.e. the instrument can be moved up and down in the canal; rotational; vibrational, i.e. the instrument can be caused to vibrate by connecting it to, for example, an ultrasound transducer; or a combination of these motions. In the preferred embodiment of the invention the SAF is rotated either manually or by means of a dental handpiece. As the instrument rotates, the SAF's super elastic property keeps its elements pressed against the root canal wall in all the radial planes along the length of the instrument.

Figure 8A:
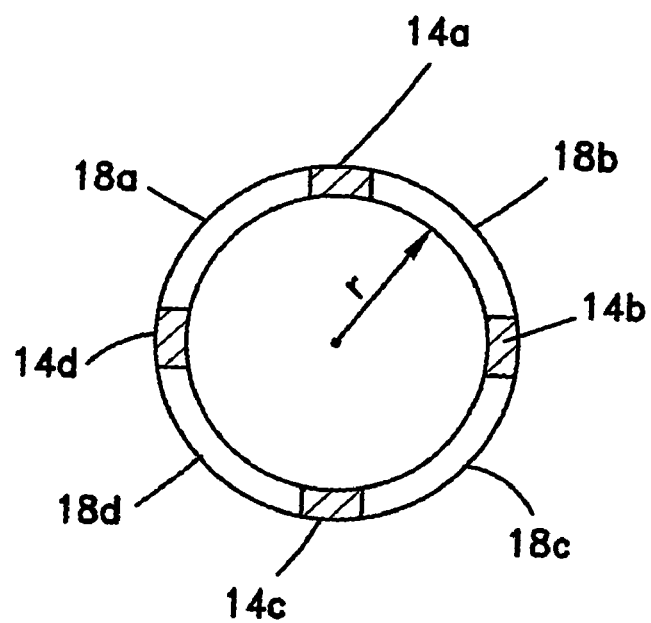
FIGS. 8A and 8B show cross-sectional views of the instrument of the invention before being inserted into the root canal and inside a tear shaped canal respectively.
Figure 8B:
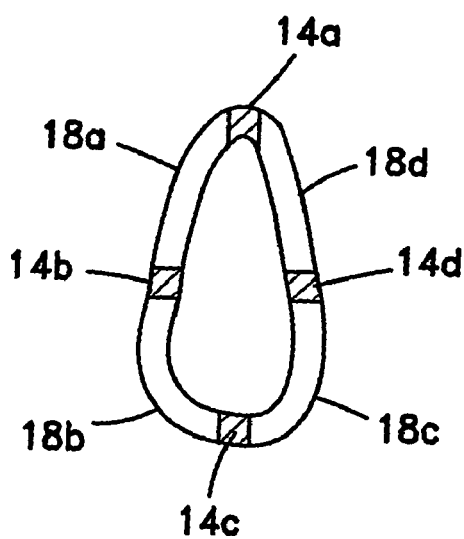

FIGS. 8A and 8B show cross-sectional views of the instrument of the invention outside of and inside a tear shaped root canal respectively. The views in the cross-sections shown in FIGS. 8A and 8B are in radial planes wherein each such radial plane is located at and contains a single set of circumferential elements. Since the axis of the SAF essentially lies on the longitudinal axis of the canal, each plane intersects the walls of the canal at right angles. The perimeter of the SAF in each of these planes is made up of eight segments—14a to 14d, the longitudinal elements, and 18a to 18d, the circumferential elements. The material and structure of the SAF have three properties that allow it to carry out the desired function. Firstly, the superelasticity of the alloy makes the device constructed from it extremely flexible, allowing it to be deformed to conform to the shape of the canal at the position at which it is located. Secondly, the diameter of the original cylindro-conic state of the instrument is greater than the diameter of the canal. Therefore the stress created in the alloy by the deformation from contact with the walls of the canal as the instrument is rotated and the super elastic property causing the instrument to try to return to its original cylindro-conic shape. The internal force exerted in attempting this return to the original shape constantly pushes the elements of the device against the inner wall of the canal. Thirdly each element made of the super elastic alloy has the property of being able to stressed/strained up to 8% to 10% from it's original shape, depending on the exact composition of the alloy, thus allowing the internal volume of the SAF to increase with time and its elements to remain in constant contact with the walls, even as material is continually being removed from them. As the instrument rotates each of the circumferential elements 18a to 18d changes in length and shape independently from the others, thus the instrument is able to conform to the local shape of the canal wall.

The fact that the circumference of the instrument is divided into four elements, each of which can independently change shape imparts to the SAF a degree of flexibility, an ability to adapt to the shape of the root canal, and the ability to expand in size that goes far beyond that of existing files. These properties can be further increased by building the instrument with a greater number of peripheral elements, however increased flexibility, etc. will be gained at the expense of the strength of the device.

Thus, in the plane shown, as the instrument rotates, its cross-sectional shape is constantly changing to conform to the shape of the canal wall and the length of the circumference of the device in that plane is constantly increasing as material is removed from the wall. This is to be compared to the situation with existing files in which the shape of the canal is changed to conform to the shape of the file and the files must constantly be replaced with files of larger diameter in order to clean, widen, and shape the canal.

The description given hereinabove applies for each successive set of circumferential elements located in different radial planes along the length of the instrument. The adaptation to the local shape of the canal and changes in contour and length of the circumferential elements that comprise each successive set is essentially independent of its neighbors. This behavior explains how the instrument of the invention can deal with the common situation described hereinabove in which the canal narrows along much of its length and then becomes wide near the apical tip before narrowing again. Because the instrument is moved (rotated) as a single unit, the amount of material removed from the canal wall, which mainly depends on how long the instrument is revolved, is essentially constant along the entire length of the portion of the instrument that is inserted into the canal.

For almost all cases, the deviations of the diameter of the root canal from its average diameter are such that the instrument of the invention can be designed to allow use of a single instrument to clean out the whole length of the canal. In the preferred embodiments of the invention, the outer surface of the instrument is uniformly treated to enable removal of material from the wall, in which case essentially the same amount of material will be removed from the wall of the canal at each radial plane along its entire length. However, the skilled person will know how the instrument can be designed and treated to allow non-uniform removal of material at different positions along the length of the canal, if this result is desired for specific applications. Based on statistical information regarding the dimensions of root canals from a large number of teeth, a single nominal width can be determined for the instrument of the invention. It may be however, that it is preferable to provide instruments having several different nominal diameters, for example a small diameter for a narrow canal and a larger diameter for wide canals. In any case, once the correct size instrument has been selected, the entire cleaning, widening, and shaping procedure is then carried out using only that instrument which, once inserted into the canal, is only withdrawn at the end of the procedure. It is to be noted that in some cases, the channel to be worked on by the instrument of the invention may have an exceptionally widely varying cross section, in which case more than one instrument, having different nominal diameters, will have to be used to shape, widen, and clean the entire channel.

Figure 1:
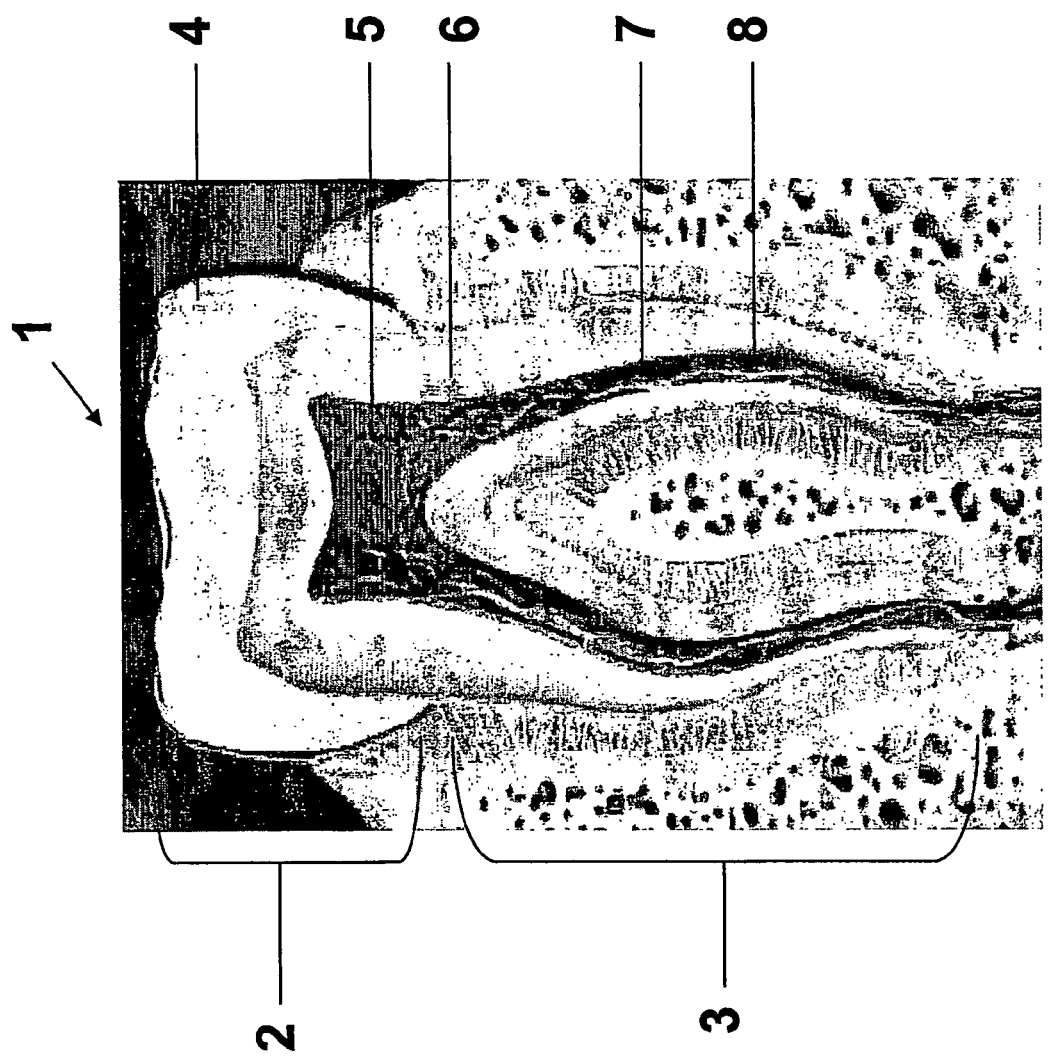
FIG. 1 shows the anatomy of a tooth.
Figure 2A:
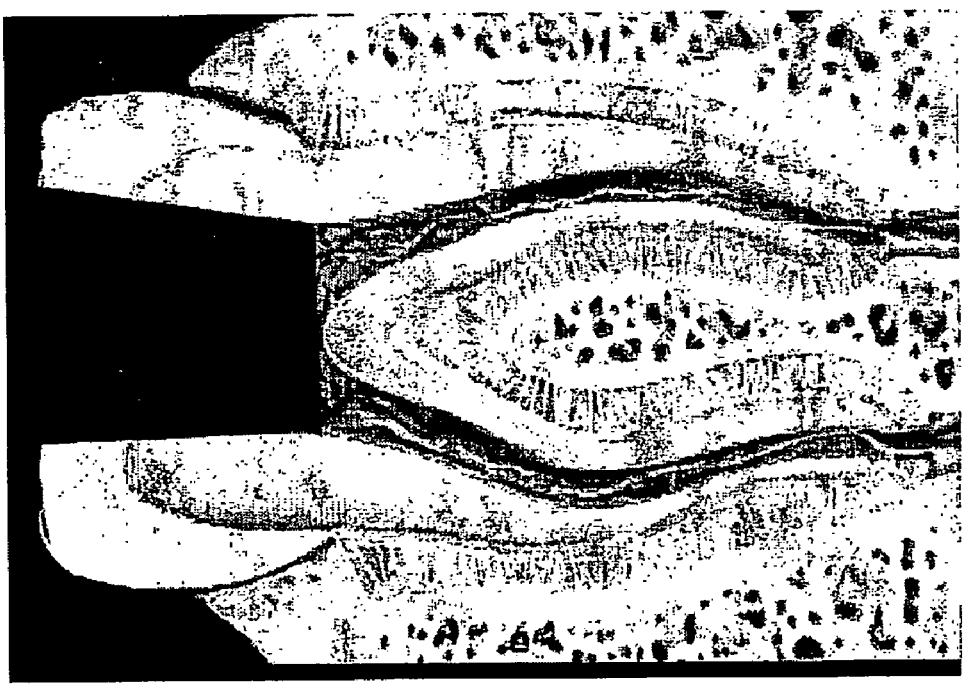
FIGS. 2A to 2C illustrate the major steps of the root canal procedure.
Figure 2B:
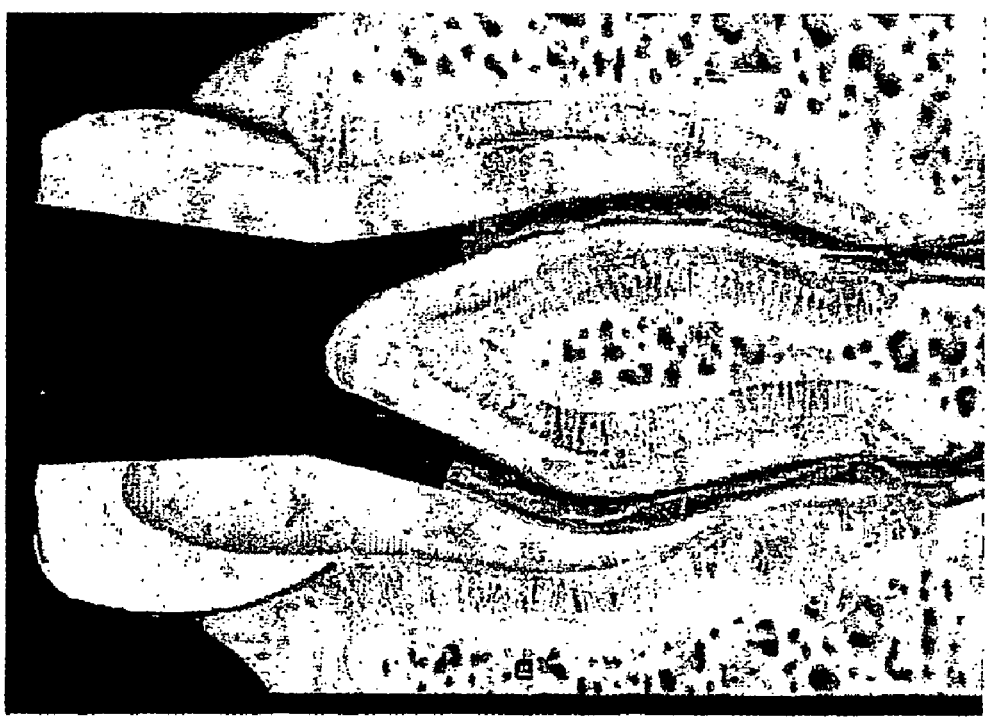
Figure 2C:
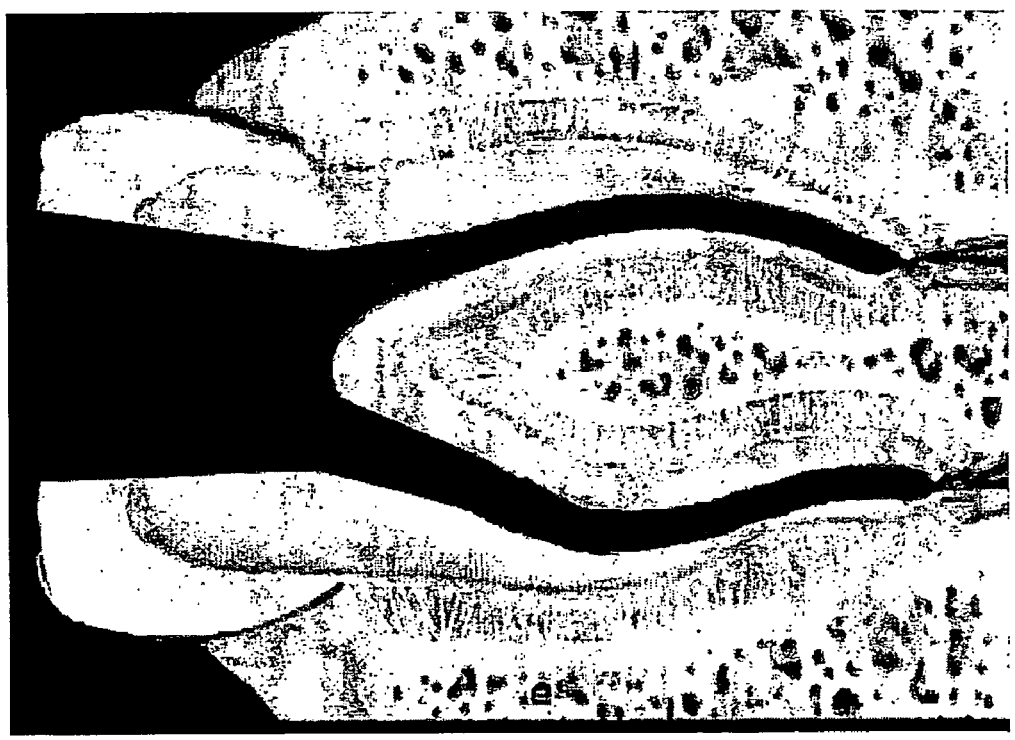
Figure 3A:
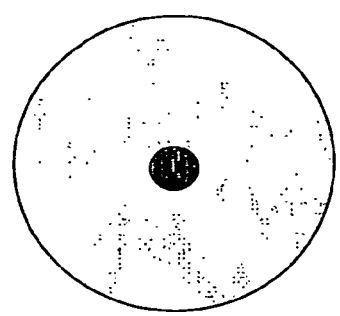
FIGS. 3A to 3C show root canals having different cross sectional shapes.
Figure 3B:
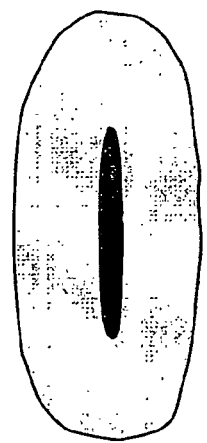
Figure 3C:
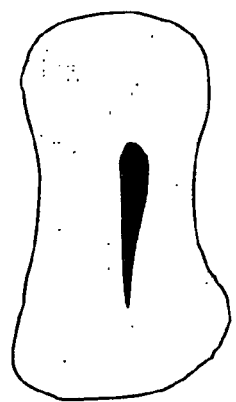
Figure 4:
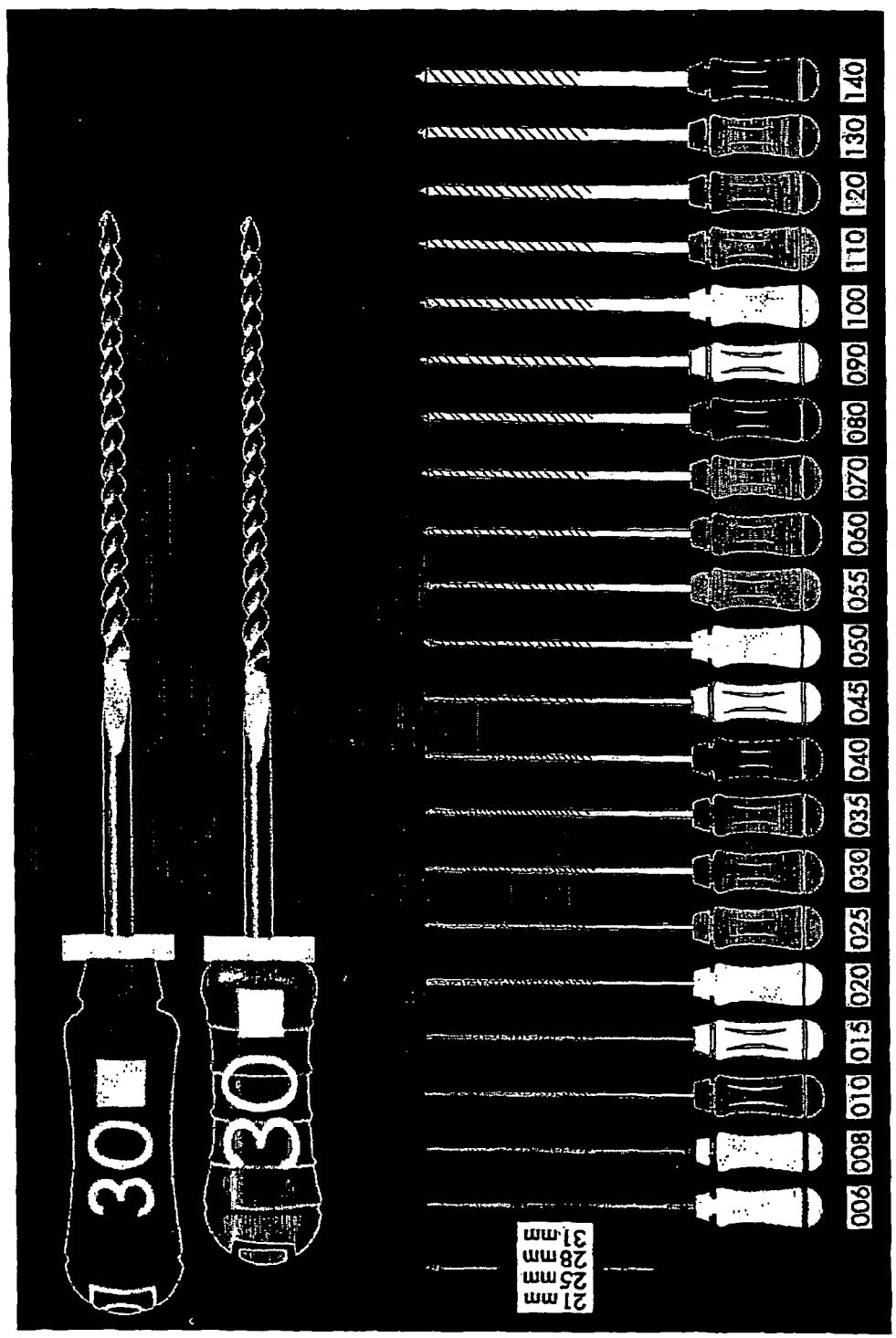
FIG. 4 shows a set of stainless steel K-files.
Figure 5A:
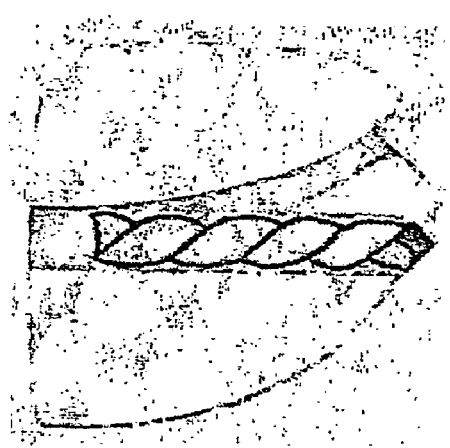
FIGS. 5A to 5D show some of the problems encountered in using prior art files to perform root canal treatments.
Figure 5B:
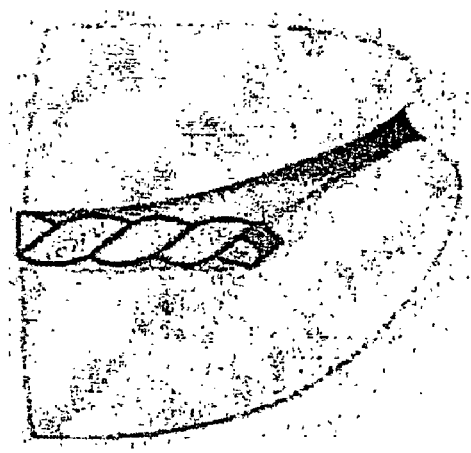
Figure 5C:
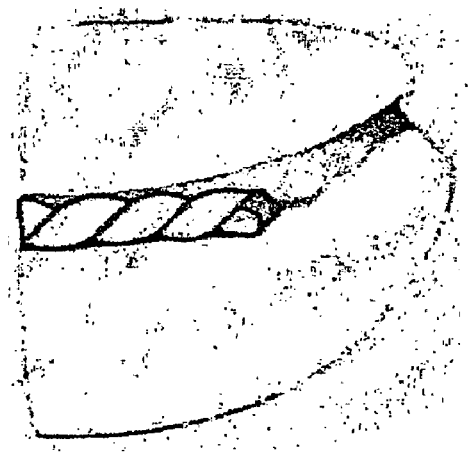
Figure 5D:
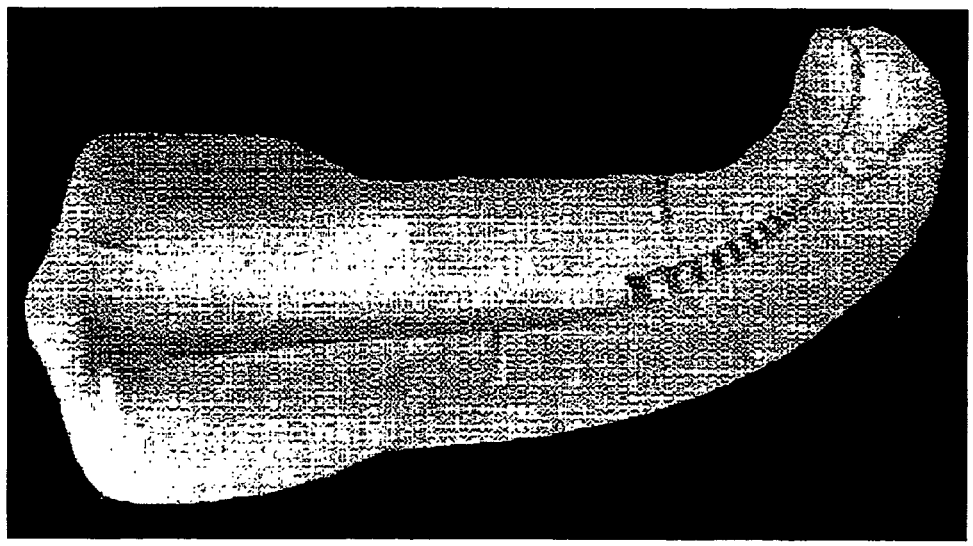
Figure 6A:
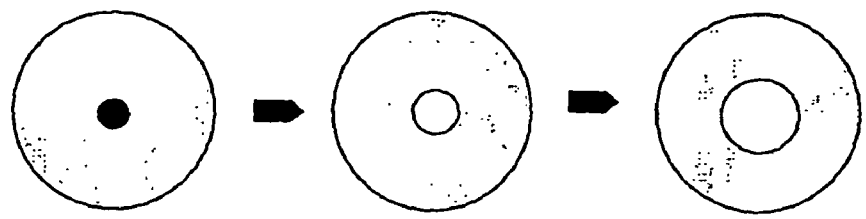
FIGS. 6A to 6C show the stages, according to the prior art, in preparing root canals having different cross sectional shapes.
Figure 6B:
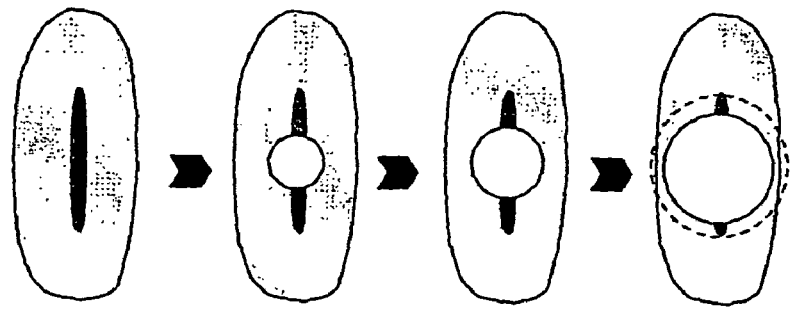
Figure 6C:
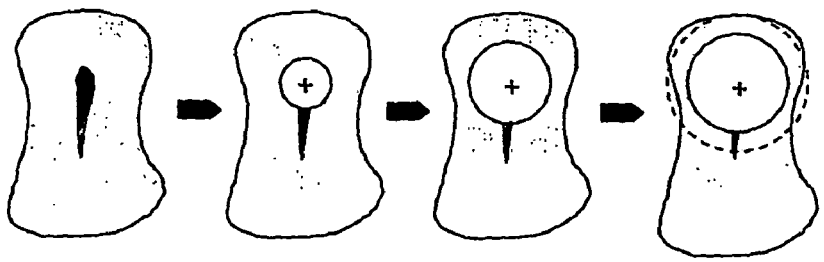
Figure 9A:
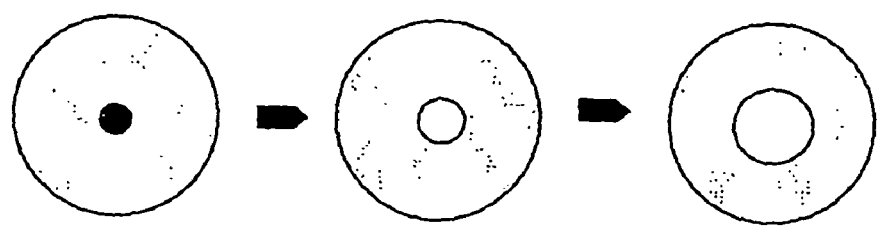
FIGS. 9A, 9B, and 9C show schematically the preparation of a root canal, using the self adjusting instrument of the invention, for root canals having round, flat, and tear-shaped cross-sections respectively.
Figure 9B:
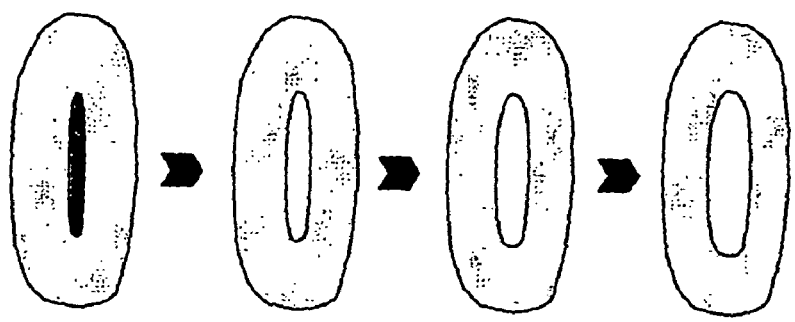
Figure 9C:
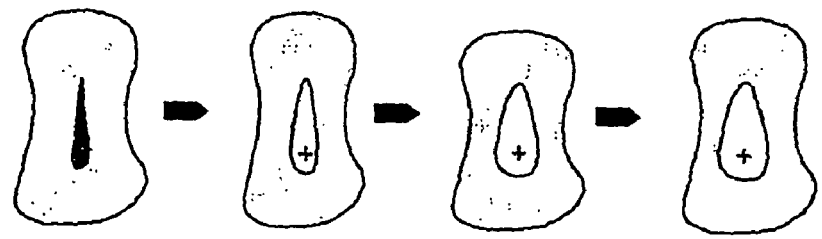

The preparation of a root canal, using the self adjusting instrument of the invention is shown schematically FIGS. 9A, 9B, and 9C for root canals having round, flat, and tear-shaped cross-sections respectively. The figures are a series of images showing the stages of the cleaning, shaping, and widening step in the procedure. The images range from the untreated root canal on the left to the canal at the end of the procedure on the right. From the figures, it can be seen that the rotating SAF removes a relatively uniform layer from all inner surfaces of the canal wall and therefore the final shape of the cleaned out canal (right image) is very close to that of the original canal. The shaping and widening are done by removing a minimal amount of the canal wall and therefore without causing localized thinning of the root wall as is the case in the prior art (see FIGS. 6B and 6C). Using the SAF to clean out the root canal, the nominal diameter and shape of the canal at each radial plane along its length is preserved. In other words the shaped and cleaned canal does not have an essentially circular cross section having a uniform cross-sectional area along its length as is the case with the prior art.

Shaping, widening, and cleaning the root canal with one instrument, while flushing with a constant flow of antiseptic solution, may significantly cut down treatment time. Additionally shaping and cleaning the root canal with one instrument eliminates the necessity of the operator following complex and tricky flow charts in order to accomplish a simple root canal treatment procedure, as is demanded by current leading rotary file systems.

Heat-softened gutta-percha methods can be easily adapted for obturation of the prepared root canal obtained with the instrument of the invention.

Many variations in the choice of materials and especially in the design of the structure of the device are possible. For example, the device does not have to be built from Nitinol but other types of material, such as, for example, stainless steel, steel, plastic, nickel based alloys, and titanium based alloys can be chosen. Instead of having circumferential and longitudinal elements with a flat rectangular blade-like shape as described hereinabove the elements can have, for example, polygonal prism, rod-like, or curved shapes. Similarly, elements having polygonal (including rectangular, square and triangular), round, and curved cross sections can be used. The combination of original cylindrical shape of the instrument and cylindrical-conic shape after heat treatment, which is most suitable for root canal work, can be replaced by other shapes which might be more suitable for specific applications. Additionally the structure of the instrument need not be the same as the preferred embodiment of the SAF described hereinabove. FIGS. 11A to 11F show cross-sections of some examples of different embodiments of the instrument of the invention. The longitudinal elements are designated by numeral 20 and the circumferential elements 21. FIG. 11A shows the SAF and FIG. 11B is a similar design except that, in this embodiment, only the outer surfaces of the longitudinal elements are in contact with the canal wall. Using the embodiment of FIG. 11B, the debris can be removed upwards through the space between the canal wall and the circumferential elements while fluid flows downwards through the center of the device, or vice versa. The embodiment of FIG. 11C is triangular shaped. The longitudinal elements can be round and covered with abrasive material or teeth or they can be triangular shaped with the outward facing apex acting as a cutting/scraping edge. The embodiment shown in FIG. 11D has a single square longitudinal element with four blades attached to it. The embodiments of FIG. 11E and FIG. 11F have a single longitudinal element from which project radially a multitude of blade-like or wire-like elements. The means of designing and manufacturing these and other embodiments of the instrument of the invention, including providing the necessary superelastic and shape memory properties is within the scope of the knowledge of skilled persons and therefore will not be discussed in further detail herein.

In another embodiment, the instrument of the invention comprises a long narrow balloon, which is inserted into the channel and then inflated. This embodiment can be realized in several ways. For, example, an instrument based on the design of the SAF can be built in which the circumferential elements are removed and a balloon is mounted to the device along its longitudinal axis and inside the longitudinal elements. The balloon is attached to the device at the neck and to the distal ends of the longitudinal elements. The instrument is inserted into the canal with the balloon deflated. When in position, fluid is introduced into the interior of the balloon using conventional techniques and the balloon expands pushing the longitudinal elements against the walls of the channel. The outer surfaces of the longitudinal elements are treated or shaped in some way to enable them to remove material from the wall as the instrument is moved relative to the walls of the channel. With embodiments comprising a balloon, the relative motion is preferably translational, i.e. the instrument is alternately pushed and pulled in the direction of the longitudinal axis of the channel.

In an alternate embodiment, the device can comprise a balloon only which is coated with an abrasive material on its outer surface. To give the balloon sufficient rigidity, a rod or wire is inserted into the interior of the balloon and attached at the distal end. The balloon is inserted into the channel and then inflated pressing the sides of the balloon against the walls of the channel. The relative motion is preferably translational i.e. pushing and pulling the internal rod in the direction of the longitudinal axis of the channel will cause the balloon to move relative to the wall cleaning, shaping, and widening the channel. When the work is completed, the balloon is deflated and withdrawn from the channel.

Although embodiments of the invention have been described by way of illustration, it will be understood that the invention may be carried out with many variations, modifications, and adaptations, without departing from its spirit or exceeding the scope of the claims.

BIBLIOGRAPHY

1. Saunders, W P, Saunders, E M, Sadiq, J, Cruickshank, E, Technical standard of root canal treatment in an adult Scottish sub-population, Br Dent J 182: 382-386, 1990.
2. Wu, M-K, R'oris, A, Borkis, D, Wesselink, PR, Prevalence and extent of long oval canals in the apical third, Oral Surg Oral Med Oral Pathol 89:739-743, 2000.
3. Tan, BT, Messer, H H, The quality of apical canal preparation using hand and rotary instruments with specific criteria for enlargement based on initial apical file size, J Endodon 28: 658-664, 2002.
4. Wu, M-K, Wesselink P R, A primary observation on the preparation and obturation of oval canals, In. Endod J 34:137-141, 2001.

The invention claimed is:

1. An endodontic instrument for removing material from a wall of a root canal channel, the instrument comprising
   a hollow flexible member having a longitudinal axis and an initial cross-sectional area in a plane perpendicular to the longitudinal axis at each point along the longitudinal axis,
   the member comprising a wall having an open lattice-like structure surrounding a hollow interior portion of the instrument, said open lattice structure comprising a plurality of longitudinal elements extending generally parallel to the longitudinal axis, and a plurality of connecting elements interconnecting between said longitudinal elements,
   the member being bendable along the axis and resiliently compressible in cross-sectional area such that, when inserted into a channel of cross-sectional area less than the initial cross-sectional area, the flexible member conforms to an internal shape of the channel.

2. The endodontic instrument of claim 1, wherein the flexible member is a shape memory member.

3. The endodontic instrument of claim 1, further comprising a cutting edge on at least a portion of an exterior surface of the member.

4. The endodontic instrument of claim 1, further comprising on at least a portion of an exterior surface of the member at least one selected from a group consisting of an abrasive surface, a roughened surface, small teeth, and a cutting edge.

5. The endodontic instrument of claim 4, wherein the instrument is made from one selected from a group consisting of a superelastic material, a material having shape memory properties, and a material treated to give the material shape memory properties.

6. The endodontic instrument of claim 4, wherein the instrument is made from a nickel titanium alloy.

7. The endodontic instrument of claim 1, wherein, in an uncompressed state of the flexible member, said longitudinal elements and said connecting elements lie substantially on a cylindrical profile.

8. The endodontic instrument of claim 7, wherein said longitudinal elements and said connecting elements define an open structure such that a majority of an area of said cylindrical profile is open.

9. The endodontic instrument of claim 7, wherein at least part of each of said connecting elements extends in a direction having a longitudinal component.

10. The endodontic instrument of claim 1, wherein the flexible member is resiliently compressible such that, when the flexible member is rotated about said longitudinal axis, the flexible member remains pressed against an internal surface of a non-circular channel.

11. The endodontic instrument of claim 1, wherein the channel is non-circular in cross-sectional shape.

12. An endodontic instrument for removin material from a wall of a root canal channel, the instrument comprising:
  a hollow flexible member having a longitudinal axis and an initial cross-sectional area in a plane perpendicular to the longitudinal axis at each point along the longitudinal axis,
  the member comprising a wall having an open lattice-like structure surrounding a hollow interior portion of the instrument,
  the member being bendable along the axis and resiliently compressible in cross-sectional area such that when inserted into a channel of cross-sectional area less than the initial cross-sectional area the flexible member conforms to an internal shape of the channel,
  wherein at least a portion of an exterior surface of the member comprises at least one selected from a group consisting of: an abrasive surface a roughened surface, small teeth, and a cutting edge,
  and wherein said open lattice-like structure comprises at least one longitudinal element connected to a plurality of circumferential elements.

13. The endodontic instrument of claim 12, wherein the circumferential elements are straight elements.

14. The endodontic instrument of claim 12, wherein the longitudinal element is one selected from a group consisting of a straight element and a curved element, and wherein the circumferential elements are selected from a group consisting of straight elements and curved elements.

15. An endodontic instrument for removing material from a wall of a root canal channel, the instrument comprising
  a hollow flexible member having a longitudinal axis and an initial cross-sectional area in a plane perpendicular to the longitudinal axis at each point along the longitudinal axis,
  the member comprising an open lattice-like structure comprising a plurality of longitudinal elements extending generally parallel to the longitudinal axis, and a plurality of connecting elements interconnecting between said longitudinal elements, said longitudinal elements and said connecting elements together defining an external profile of the member, a majority of an area of said external profile being open,
  the member being bendable along the axis and resiliently compressible in cross-sectional area such that, when inserted into a channel of cross-sectional area less than the initial cross-sectional area, the flexible member conforms to an internal shape of the channel.

16. The endodontic instrument of claim 15, wherein the flexible member is a shape memory member.

17. The endodontic instrument of claim 15, further comprising on at least a portion of an exterior surface of the member at least one selected from a group consisting of an abrasive surface, a roughened surface, small teeth, and a cutting edge.

18. The endodontic instrument of claim 15, wherein said longitudinal elements and said connecting elements together form an open lattice structure.

19. The endodontic instrument of claim 15, wherein the instrument is made from one selected from a group consisting of a superelastic material, a material having shape memory properties, and a material treated to give the material shape memory properties.

20. The endodontic instrument of claim 15, wherein the instrument is made from a nickel titanium alloy.

21. The endodontic instrument of claim 15, wherein, in an uncompressed state of the flexible member, said longitudinal elements and said connecting elements lie substantially on a cylindrical profile.

22. The endodontic instrument of claim 15, wherein at least part of each of said connecting elements extends in a direction having a longitudinal component.

23. The endodontic instrument of claim 15, wherein the flexible member is resiliently compressible such that, when the flexible member is rotated about said longitudinal axis, the flexible member remains pressed against an internal surface of a non-circular channel.

* * * * *